US00PP27469P3

(12) United States Plant Patent
Layt

(10) Patent No.: US PP27,469 P3
(45) Date of Patent: Dec. 20, 2016

(54) ***GREVILLEA ROSMARINIFOLIA* PLANT NAMED 'H16'**

(50) Latin Name: *Grevillea rosmarinifolia*
Varietal Denomination: H16

(71) Applicant: Todd Anthony Layt, Richmond (AU)

(72) Inventor: Todd Anthony Layt, Richmond (AU)

( * ) Notice: Subject to any disclaimer, the term of this patent is extended or adjusted under 35 U.S.C. 154(b) by 153 days.

(21) Appl. No.: 14/120,125

(22) Filed: Apr. 28, 2014

(65) Prior Publication Data

US 2015/0313052 P1 Oct. 29, 2015

Related U.S. Application Data

(60) Provisional application No. 61/817,467, filed on Apr. 30, 2013.

(51) Int. Cl.
*A01H 5/02* (2006.01)

(52) U.S. Cl.
USPC ..... Plt./226

(58) Field of Classification Search
USPC ..... Plt./226
CPC ..... A01H 5/02; A01H 5/00
See application file for complete search history.

(56) References Cited

PUBLICATIONS

Ozbreed Encironmental Turf and Plant Breeding Blog, posted May 31, 2012, retrieved on Oct. 14, 2015, retireved from the Internet at <https://ozbreed.wordpress.com/2012/05/31/crimson-villea-mass-plantings-specimen-plantings-for-native-gardens-and-rockeries/> pp. 1-2.*

Youtube. Branching compact with masses of flowers Crimson Villea, uploaded Aug. 31, 2011, retrieved on Oct. 14, 2015, retrieved from the Internet at <https://www.youtube.com/watch?v=mmAUdY9RMGs> 2 pp.*

* cited by examiner

*Primary Examiner* — June Hwu
(74) *Attorney, Agent, or Firm* — Samuel R. McCoy, Jr.

(57) ABSTRACT

'H16' is a distinctive variety of *Grevillea rosmarinifolia* which is characterized by the combination of a denser plant habit and a greater number of inflorescences per plant.

3 Drawing Sheets

Latin name of the genus and species: The Latin name of the genus and species of the novel variety disclosed herein is *Grevillea rosmarinifolia.*

Variety denomination: The inventive variety of *Grevillea rosmarinifolia* disclosed herein has been given the variety denomination 'H16'.

BACKGROUND OF THE INVENTION

The present invention relates to a new and distinct perennial variety of *Grevillea rosmarinifolia*, which has been given the variety denomination of 'H16'. *Grevillea rosmarinifolia* is a well-known Australian native species, which usually occurs as a small to medium rounded shrub growing to a mature height of approximately 0.3 to 2.0 meters high. In the United States, *Grevillea* is typically used in commercial and residential landscaping in arid climates. The common name of this species is Rosemary *Grevillea*. Its market class is that of an ornamental plant. 'H16' is intended for use in landscaping and as a decorative plant.

Parentage: 'H16' is a seedling selection discovered in 2003 which resulted from the open pollination of *Grevillea rosmarinifolia* (unnamed and unpatented) and *Grevillea* 'Scarlet Sprite' (unpatented) in a nursery operation in Clarendon, New South Wales, Australia. Seed was collected, and subsequently germinated, from both the *Grevillea rosmarinifolia* plants and also the *Grevillea* 'Scarlet Sprite' plants. The cultivar now called 'H16' was isolated from other progeny because it was easily observed to have a more compact and dense growth habit when compared to siblings.

The candidate seedling was grown to a mature growth stage where it was confirmed to have a more dense foliage and growth habit compared to one of its probable parent *Grevillea* 'Scarlet Sprite'. The new and distinct variety was named 'H16'.

Asexual Reproduction: 'H16' was first asexually reproduced by way of softwood stem cuttings in spring 2007 at a nursery operation in Clarendon, New South Wales, Australia to see if it grew true to type. It was found to grow uniform and reproduce in a stable manner and 6 successive cycles of vegetative propagation have proven to be true to type also.

SUMMARY OF THE INVENTION

'H16' is a distinctive variety of *Grevillea rosmarinifolia* which is characterized by the combination of a denser plant habit and a greater number of inflorescences per plant.

BOTANICAL DESCRIPTION OF THE PLANT

Figure 1:
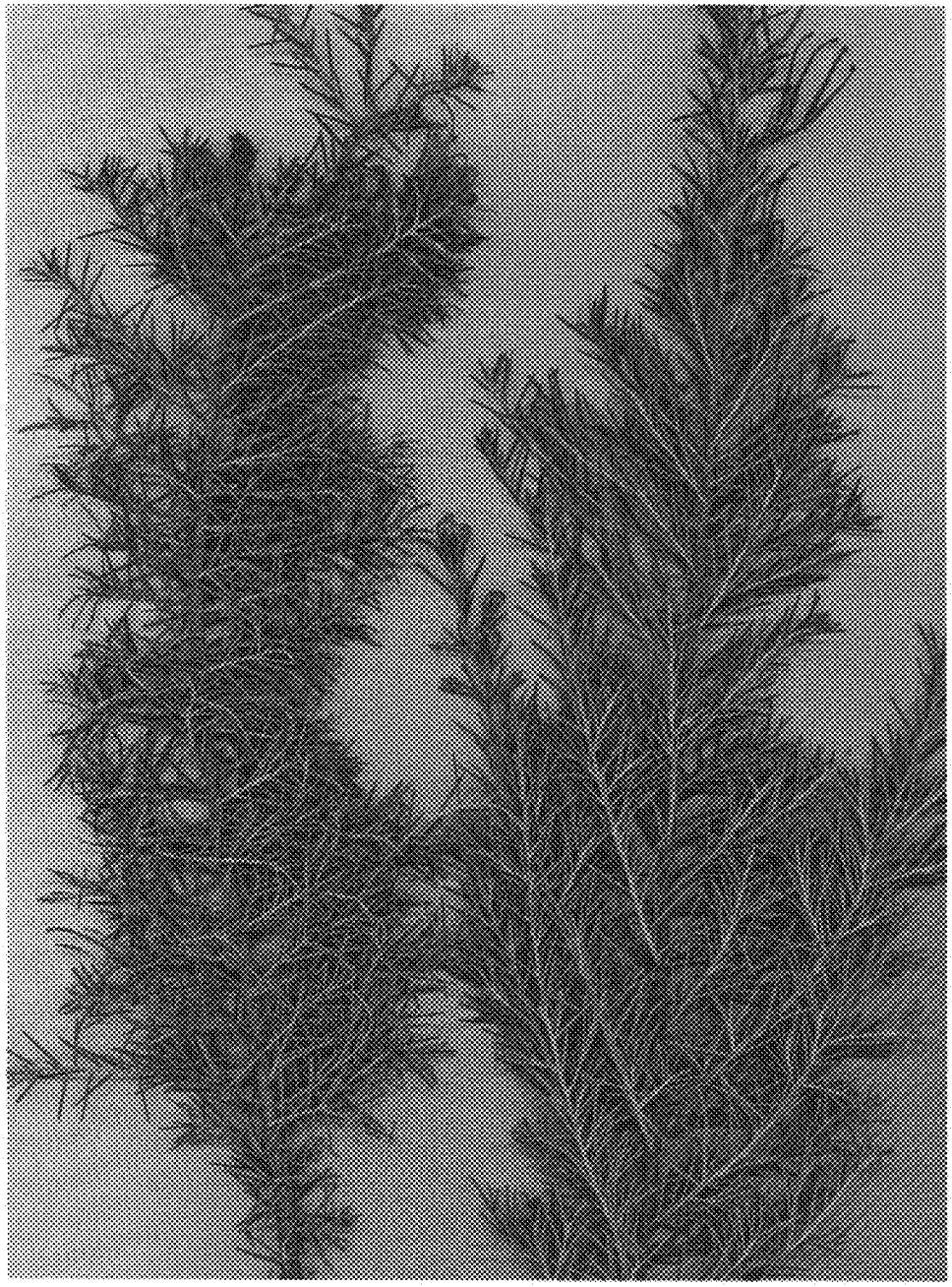
FIG. 1 shows a comparison of the secondary branching between 'H16' and comparator, *Grevillea rosmarinifolia* 'Scarlet Sprite'
Figure 2:
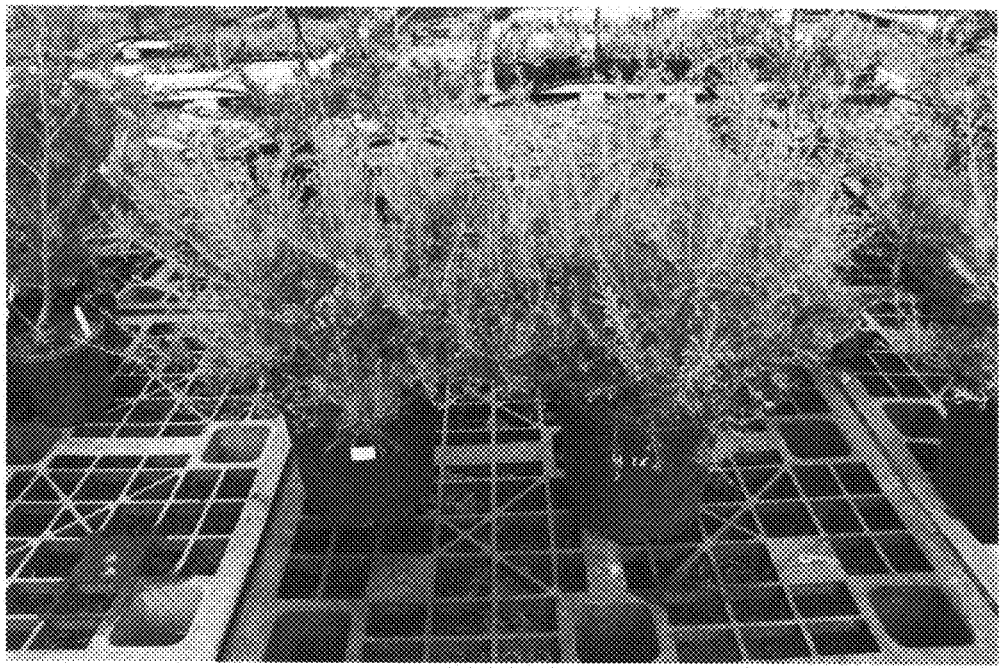
FIG. 2 shows the difference in plant growth density between a mature 'H16' plant, on right, and comparator 'Scarlet Sprite' on left.
Figure 3:
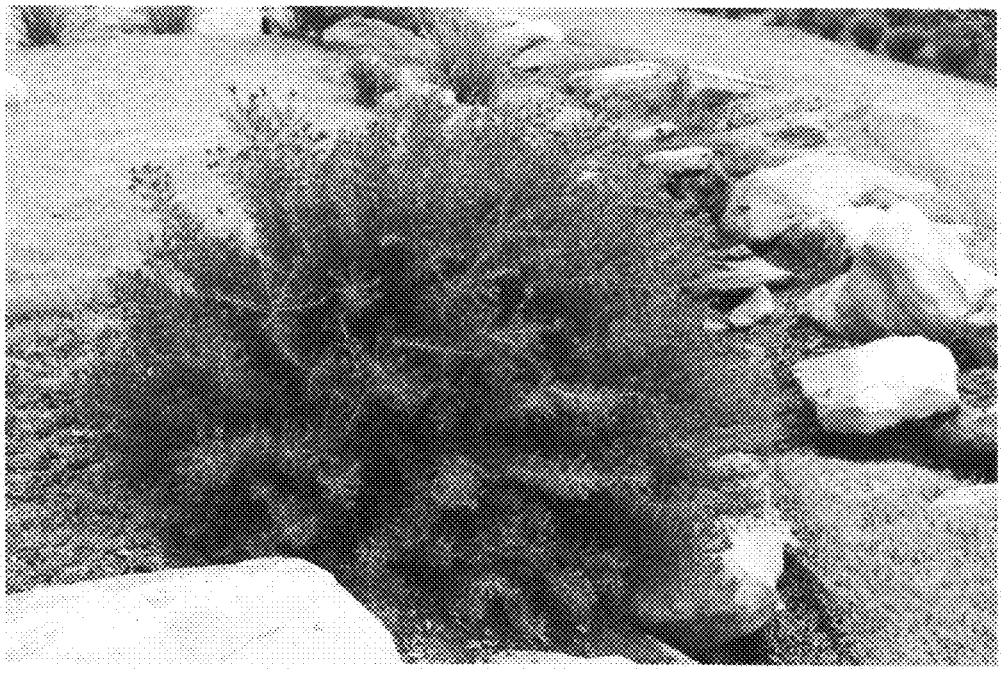
FIG. 3 shows an exemplary mature specimen of a 'H16' plant, established in the landscape.

The following is a detailed botanical description of a new and distinct variety of a *Grevillea rosmarinifolia* ornamental plant known as 'H16'. Plant observations were made on plants grown in New South Wales, Australia. Unless indicated otherwise, the descriptions disclosed herein are based upon observations made from 3 year-old mature 'H16' plants grown in full sun from rooted cuttings in 400 mm nursery pots filled with soilless potting media, maintained with granular slow release fertilizer and regularly watered with overhead irrigation. No pest and disease measures were taken. Observation data was recorded in the spring of 2011.

Those skilled in the art will appreciate that certain characteristics will vary with older or, conversely, younger plants. 'H16' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'white' do not exist in the R.H.S. charts and the corresponding R.H.S. colors are quoted.

Growth Habit, Dimensions and Color

Plant description:

*Plant habit*.—Shrub, rounded and very dense.

*Height*.—Approximately 100 cm.

*Width*.—Approximately 100 cm.

*Bloom period*.—Winter through spring and sporadically in fall and winter in warmer climates.

*Hardiness*.—USDA Zone 9 to 11.

*Environmental tolerances*.—'H16' has not yet been observed under all conditions but has shown to be heat tolerant, adapting well to temperatures of 103 degrees Fahrenheit without any noticeable damage. It has survived light to moderate frosts and temperatures down to 25 degrees Fahrenheit.

*Drought tolerance*.—'H16' has not yet been observed under all conditions but it has shown good drought tolerance typical of the species once established.

*Pest and disease susceptibility or resistance*.—In common with the species, none of note.

*Propagation*.—Propagation is accomplished using softwood cuttings. Roots well using rooting hormone compounds.

*Time to develop roots*.—3 to 4 weeks.

*Crop time*.—From 9 to 12 months are needed to produce a 14-centimeter container with plant in flower, starting from a rooted cutting, depending on geographic location.

Stems: Freely-branched with many secondary branches; orientation is upward and outward creating a round plant shape. Stem shape is cylindrical; texture is corky; the color of immature stems is closest to greyed-yellow 199D (R.H.S. 1986 edition); the color of mature stems is described as a combination of grey-brown 199C (R.H.S. 1986 edition) to brown 200D (R.H.S. 1986 edition). Internode length averages 5.9 mm. Average length of secondary branches is 12.2 cm.

Leaf: Arrangement is whorled and leaf attachment is sessile. Shape is acicular, or needle-like; apex is acute; margin is entire. Upper surface is glabrous and lower surface is pubescent. Average length is 17 mm and the average width is 1.0 mm. Color of both the adaxial and abaxial surfaces are green corresponding to RHS 141A.

Roots: Clusters of closely spaced short lateral rootlets.

Inflorescence: Apical and axillary racemes with small clusters of approximately 16 to 22 flowers; dimensions vary but a mature terminal raceme is approximately 70 to 80 mm in length, from the base of the peduncle to the stigma of the terminal-most flower, and approximately 65 to 75 mm wide, from style to style of the most outstretched lateral flowers. Flower opening sequence can be described as racemose.

Flowers: Small, pedicellate floret (pedicels of approximately 5 to 10 mm long, depending on age) with a closed perianth which creates a floral tube made up of two dorsal and two ventral tepals, which terminate at their apex and form a ball-like "tepal limb" which house the anthers. A relatively long, curved and pronounced pistil emerges from the dorsal tepals. Perianth, style and stigma colors are red RHS 46A; pollen presenter color approximates to yellow green 154D (R.H.S. 1986 edition). Perianth tube width averages 5.2 mm with an average length of 22 mm, including the outstretched style. The perianth surfaces and ovary are smooth, with medium pubescence and a matte luster. Nectaries are approximately 1.5 mm; color is red RHS 46A.

Fruit and seed: To date, all flowers observed have aborted prior to follicle development.

Comparison of H16 with Other Varieties of *Grevillea rosmarinifolia*

Several of *Grevillea rosmarinifolia* varieties were initially compared to 'H16' but were ultimately excluded as comparators for one or more reasons. It was determined that the most similar variety of common knowledge was, in fact, the supposed seed parent, *Grevillea rosmarinifolia* 'Scarlet Sprite'. Both have a similar growth habit and plant shape and both have a similar flower color and bloom habit. However, by comparison, 'H16' exhibits more vigorous branching which translates to a denser growth habit and more inflorescences per plant.

With respect to branching vigor, based on observations and data collected in spring 2011 from 12 random branches on 3 year old plants grown in 400 mm nursery pots in full sun, 'H16' had, on average, 5.6 secondary branches of more than 10 cm in length. By comparison, 'Scarlet Sprite' plants of the same age had, on average, only 1 secondary branch of more than 10 cm in length. Refer to FIG. 1 for an illustration of this observation. Because these secondary branches subsequently give rise to tertiary branches, it stands to conclude that a plant with longer secondary branches like 'H16' has a denser plant habit. These longer secondary branches also translate into a greater number of inflorescences per plant as axillary inflorescence of *Grevillea rosmarinifolia* occur along the entire length of these secondary branches.

Furthermore, measurements were taken from the 10 of the longest secondary branches of five individual plants of both 'H16' and 'Scarlet Sprite'. The data collected shows that from the measured, the longest secondary branches of 'H16' had an average length of 12.2 cm whereas the average length of the longest secondary branches of 'Scarlet Sprite' was 8.04 cm. This data further supports the assertion that 'H16' has a denser growth habit and a greater number of inflorescences per plant.

The combination of a denser plant habit and a greater number of inflorescences makes 'H16' a desirable ornamental plant suited for mass production for pot and landscape use.

That which is claimed is:

1. A new and distinct variety of *Grevillea rosmarinifolia* plant named 'H16', substantially as described and illustrated herein.

* * * * *